United States Patent
Murata

(10) Patent No.: US 9,642,864 B2
(45) Date of Patent: May 9, 2017

(54) METHOD FOR ADJUSTING DRUG RELEASE LEVEL FROM THE INTRACHOROIDAL IMPLANT AND METHOD FOR THE TREATMENT USING THE INTRACHOROIDAL IMPLANT

(71) Applicant: Masatoshi Murata, Morioka (JP)

(72) Inventor: Masatoshi Murata, Morioka (JP)

( * ) Notice: Subject to any disclaimer, the term of this patent is extended or adjusted under 35 U.S.C. 154(b) by 211 days.

(21) Appl. No.: 14/153,655

(22) Filed: Jan. 13, 2014

(65) Prior Publication Data
US 2014/0221904 A1    Aug. 7, 2014

(30) Foreign Application Priority Data

Feb. 6, 2013 (JP) .................................. 2013-021273

(51) Int. Cl.
| | | |
|---|---|---|
| *A61K 41/00* | (2006.01) | |
| *A61F 9/00* | (2006.01) | |
| *A61K 31/573* | (2006.01) | |
| *A61N 5/06* | (2006.01) | |
| *A61K 9/00* | (2006.01) | |
| *A61K 47/34* | (2017.01) | |

(52) U.S. Cl.
CPC .......... *A61K 31/573* (2013.01); *A61K 9/0051* (2013.01); *A61K 41/0042* (2013.01); *A61K 47/34* (2013.01)

(58) Field of Classification Search
None
See application file for complete search history.

(56) References Cited

U.S. PATENT DOCUMENTS

| | | | | |
|---|---|---|---|---|
| 5,164,188 | A * | 11/1992 | Wong .................... | A61K 9/0051 424/422 |
| 2005/0244466 | A1* | 11/2005 | Whitcup et al. .............. | 424/427 |
| 2005/0244500 | A1 | 11/2005 | Whitcup et al. | |
| 2009/0196903 | A1* | 8/2009 | Kliman .......................... | 424/423 |
| 2012/0172984 | A1* | 7/2012 | Murata ................. | A61F 9/0017 623/4.1 |

OTHER PUBLICATIONS

Ramirez et al., Choroidal Vessel Wall: Hypercholesterolaemia-Induced Dysfunction and Potential Role of Statins, available at http://dx.doi.org/10.5772/47794 (2012).*

* cited by examiner

*Primary Examiner* — H. Sarah Park
(74) *Attorney, Agent, or Firm* — Manabu Kanesaka

(57) ABSTRACT

An implant for a living body is designed so that the drug release level can be adjusted to make it possible to perform treatment corresponding to the severity of disease state and the effectiveness of the drug on each individual. The implant includes a drug, and is inserted into a target part of a living body to effect sustained release of the drug, the implant including a photoactive agent that accelerates the release of the drug when irradiated with laser light. The implant is inserted into a living body, and laser light is appropriately applied to the implant to adjust the release level of the drug released into the living body. An eye disease or the like is treated using the above method.

9 Claims, 10 Drawing Sheets

•Suprachoroid implant of Wong

•Choroid implant of the present application (a)

(b)

(c)

(B)

(A)

METHOD FOR ADJUSTING DRUG RELEASE LEVEL FROM THE INTRACHOROIDAL IMPLANT AND METHOD FOR THE TREATMENT USING THE INTRACHOROIDAL IMPLANT

TECHNICAL FIELD

The invention relates to an implant for a living body (hereinafter may be referred to as "implant") that includes a drug, and is inserted into a target part of a living body to effect sustained release of the drug, a method for adjusting the drug release level from the implant, and a method for treatment using the implant.

BACKGROUND ART

An implant that includes a drug may be inserted into a target part of a living body (i.e., a human or a non-human animal) that is suffering from a disease (hereinafter abbreviated as a diseased part), and the diseased part may be treated by releasing the drug from the implant in a sustained manner. For example, when the target part is part of the eye, an implant that includes a timed-release drug may be used for the treatment of various inflammatory eye diseases and proliferative eye diseases such as exudative age-related macular degeneration (ARMD), cystoid macular edema, diabetic macular edema, uveitis, retinitis, choroiditis, proliferative vieoretinopathy, and proliferative diabetic retinopathy.

A technique disclosed in JP-T-2007-535540 has been known as a technique for treating the eye using such an implant, for example. According to the technique disclosed in JP-T-2007-535540, an implant is produced by incorporating a steroid drug such as dexamethasone in a biodegradable polymer, and placed in part (e.g., vitreous body) of the patient's eye to treat the eye disease.

JP-T-2007-535540 also discloses a technique that introduces a photoactive agent into the vein or the like after placing the implant so that the photoactive agent is localized in the blood vessels present in the diseased part of the eye, and applies laser light to the diseased part to activate the photoactive agent to directly treat the diseased part. Specifically, this technique utilizes treatment using the implant and treatment using laser light in combination.

RELATED ART DOCUMENTS

Patent Document

JP-T-2007-535540

SUMMARY OF THE INVENTION

According to the above techniques, a curing effect can be achieved through the sustained release of the steroid drug. However, it is impossible to adjust the release level of the steroid drug corresponding to the severity of eye disease and the effectiveness of the drug on each individual after the implant has been inserted. When treating the eye using laser light as described above, the laser light is applied directly to the diseased part to achieve a curing effect. However, the laser light does not contribute to an adjustment of the release level of the steroid drug.

The invention was conceived in view of the above situation. An object of the invention is to provide an implant that makes it possible to adjust the drug release level, and perform treatment corresponding to the disease state and the effectiveness of the drug on each individual. Another object of the invention is to provide a method for adjusting the drug release level that makes it possible to easily adjust the drug release level in a living body through drug delivery from an implant. A further object of the invention is to provide a method for treatment using an implant that includes adjusting the drug release level in a living body through drug delivery from an implant.

The inventor of the invention conducted extensive studies, and conceived to apply laser light to an implant instead of applying laser light to a diseased part, thereby accelerating the sustained release of the drug from the implant to promote dispersion of the drug and increase the drug level. The inventor demonstrated the above effects. The above finding makes it possible to appropriately adjust the release level of the drug included in the implant. Based on the above finding, the invention provides an implant that is designed so that the sustained release of the drug from the implant can be accelerated by applying laser light to ensure reliable drug dispersion.

According to one aspect of the invention, an implant for a living body includes a drug, and is inserted into a target part of a living body to effect sustained release of the drug, the implant including a photoactive agent that accelerates the release of the drug when irradiated with laser light. The drug may be one drug or two or more drugs selected from an anti-inflammatory drug, an antimicrobial drug, an anti-cancer drug, an analgesic drug, an antihypertensive drug, an antihyperlipidemic drug, an antidiabetic drug, and the like. Note that the drug is not limited thereto.

The implant is inserted into the target part (e.g., the skin or the internal tissue to which laser light can be applied) of a living body. The drug is released into the tissue or blood through drug delivery from the implant. When the laser light is appropriately applied to the implant, the photoactive agent included in the implant absorbs the energy from the laser light to accelerate the release of the drug. As a result, the level of the drug released from the implant increases around the implant. Therefore, the release level of the drug released into the living body can be adjusted by controlling the laser light irradiation intensity, the laser light irradiation time, the number of shots, and the like, for example. This makes it possible to perform treatment corresponding to the severity of disease and the effectiveness of the drug on each individual.

The photoactive agent may be one compound or two or more compounds selected from a porphyrin, hematoporphyrin, a hematoporphyrin derivative, pheophorbide, a pheophorbide derivative, benzoporphyrin, a benzoporphyrin derivative, bacteriochlorin, purpurin, merocyanine, porphycene, and a tricarbocyanine.

In this case, it is effective to select indocyanine green as the tricarbocyanine. Indocyanine green easily absorbs laser light, and ensures reliable release of the drug.

The target part of the living body may be part of an eye. It is particularly effective that the target part of the living body is the posterior segment of the eye. Insertion of the implant into part of an eye is not only effective for ophthalmic treatment, but is also effective for treatment of various other diseases such as a systemic inflammatory disease, rheumatism, a collagen disease, hypertension, hyperlipidemia, and diabetes. Specifically, when the drug is released into blood vessels of the eye, the drug is transferred systemically through blood. Therefore, systemic diseases other than eye diseases can be treated by adjusting the drug level in blood by employing the above configuration.

In particular, when the implant is inserted into the posterior segment of the eye, the laser light can reach the implant through the crystalline lens and the vitreous body. Therefore, the laser light can be easily applied to the implant as compared with the case where the implant is inserted into the skin or the internal tissue. Moreover, it is possible to easily visually determine the state of the implant by observing the ocular fundus. Since it is unnecessary to orally take the drug after the implant has been inserted, the implant is very effective for a person who cannot easily take a drug due to dementia, or a person who has difficulty in taking a drug due to a digestive disease, for example.

It is effective that the part of the eye is the choroid. The inventor conducted extensive studies, and found that it is effective to implement sustained release of a drug from the choroid situated adjacent to the retina so that the drug acts on the retina and the vitreous body. The inventor developed a surgical procedure for easily inserting an implant into the choroid (see US2012/0172984). The surgical procedure developed by the inventor makes it possible to easily insert an implant into the choroid by liquefying the vitreous gel in the eyeball, exposing the choroid, sucking the vitreous humor to decrease the internal pressure of the vitreous body, incising the choroid in the tangential direction, expanding the choroid through bleeding to form a space, and forming a pocket in the choroid.

After the implant has been inserted into the choroid by surgery, the drug is released into the vitreous body or blood vessels from the implant in a sustained manner. In this case, laser light is appropriately applied to the implant externally through the crystalline lens using a known laser photocoagulator used for laser light treatment, for example. The photoactive agent included in the implant absorbs the energy from the laser light to accelerate the release of the drug. As a result, the level of the drug in the vitreous body or blood vessels increases. Therefore, the release level of the drug released into the vitreous body or blood vessels (blood) can be adjusted by controlling the laser light irradiation intensity, the laser light irradiation time, the number of shots, and the like, for example. This makes it possible to perform treatment corresponding to the severity of disease and the effectiveness of the drug on each individual.

When the implant is inserted into the choroid, it is easy for laser light to position the implant as compared with the case where the implant is inserted into the sclera, whereby the drug release acceleration effect can be reliably achieved.

The implant optionally includes a steroid drug as the drug. The steroid drug may be one steroid drug or two or more steroid drugs selected from cortisone, prednisolone, fluorometholone, dexamethasone, medrysone, loteprednol, fluazacort, hydrocortisone, betamethasone, prednisone, methylprednisolone, triamcinolone hexacetonide, paramethasone acetate, diflorasone, fluocinonide, derivatives thereof, and the like. Note that the steroid drug is not limited thereto. Use of such a steroid drug is particularly effective for ophthalmic treatment.

The implant optionally includes a biodegradable polymer when using the steroid drug as the drug. The biodegradable polymer may be one biodegradable polymer or two or more biodegradable polymers selected from polylactic acid, polyglycolic acid, a lactic acid-glycolic acid copolymer, hydroxypropyl cellulose, and the like. Note that the biodegradable polymer is not limited thereto.

In the implant, the steroid drug is combined with the biodegradable polymer component. For example, the steroid drug is mixed with, bonded to, or coated with the biodegradable polymer component. The steroid drug is dissolved in and diffused into the intraocular fluid or the like due to the biodegradable polymer irrespective of whether the laser light is applied.

When the implant includes the steroid drug, the biodegradable polymer, and the photoactive agent, it is effective that the implant includes 100 to 500 parts by weight of the biodegradable polymer, and 0.02 to 2 parts by weight of the photoactive agent based on 100 parts by weight of the steroid drug.

The implant preferably includes 200 to 400 parts by weight of the biodegradable polymer, and 0.05 to 1 part by weight of the photoactive agent based on 100 parts by weight of the steroid drug. The implant more preferably includes 250 to 350 parts by weight of the biodegradable polymer, and 0.1 to 0.4 parts by weight of the photoactive agent based on 100 parts by weight of the steroid drug. The above configuration is particularly effective for ophthalmic treatment.

According to another aspect of the invention, a method for adjusting a drug release level from an implant includes inserting the implant according to one aspect of the invention into a living body, and appropriately applying laser light to the implant to adjust the level of the drug released into the living body.

According to another aspect of the invention, a method for treatment using an implant includes inserting the implant according to one aspect of the invention into a living body, and appropriately applying laser light to the implant to adjust the release level of the drug released into the living body.

When the implant has been inserted into the target part of a living body, the drug is released into (inside) the living body through drug delivery from the implant. When the laser light is appropriately applied to the implant, the photoactive agent included in the implant absorbs the energy from the laser light to accelerate the release of the drug. As a result, the level of the drug released from the implant increases around the implant. Therefore, the release level of the drug released into the living body can be adjusted by regulating the laser light irradiation intensity, the laser light irradiation time, the number of shots, and the like, for example. This makes it possible to perform treatment corresponding to the disease state and the effectiveness of the drug on each individual. It is also possible to obtain basic data for treatment by applying the above method to animals.

In this case, it is effective to apply the laser light in a pulsed manner. When the laser light is applied in a pulsed manner, it is possible to control the release level by adjusting the pulse number. Specifically, since the photoactive agent accelerates the release of the drug to a different extent corresponding to the pulse number, the level can be easily controlled by changing the pulse number.

The implant is optionally inserted into the posterior segment of an eye, and the laser light is applied to the implant externally through the crystalline lens. As described above, insertion of the implant into part of an eye is not only effective for ophthalmic treatment, but is also effective for treatment of various other diseases such as a systemic inflammatory disease, rheumatism, a collagen disease, hypertension, hyperlipidemia, and diabetes. Specifically, when the drug is released into blood vessels of the eye, the drug is transferred systemically through blood. Therefore, systemic diseases other than eye diseases can be treated by adjusting the drug level in blood by employing the above configuration.

In particular, when the implant is inserted into the posterior segment of the eye, the laser light can reach the implant through the crystalline lens and the vitreous body. Therefore, the laser light can be easily applied to the implant as compared with the case where the implant is inserted into the skin or the internal tissue other than the eye. Moreover, it is possible to easily visually determine the state of the implant by observing the ocular fundus. Since it is unnecessary to orally take the drug after the implant has been inserted, the implant is very effective for a person who cannot easily take a drug due to dementia, or a person who has difficulty in taking a drug due to a digestive disease, for example.

It is effective to insert the implant into the choroid in the posterior segment of the eye. In this case, when the drug is released from the choroid situated adjacent to the retina in a sustained manner, the drug more effectively acts on the retina and the vitreous body. When the implant is inserted into the choroid, it is easy for laser light to position the implant as compared with the case where the implant is inserted into the sclera, whereby the drug release acceleration effect can be reliably achieved.

An implant that includes the steroid drug and the biodegradable polymer is optionally used as the implant. The above configuration is particularly effective for ophthalmic treatment.

According to the invention, when the laser light is appropriately applied to the implant that has been inserted into the target part of a living body, the photoactive agent included in the implant absorbs the energy from the laser light to accelerate the release of the drug. As a result, the level of the drug released from the implant increases around the implant. Therefore, the release level of the drug released into the living body can be adjusted by regulating the laser light irradiation intensity, the laser light irradiation time, the number of shots, and the like, for example. This makes it possible to perform treatment corresponding to the disease state and the effectiveness of the drug on each individual.

DESCRIPTION OF EMBODIMENTS

Figure 1:
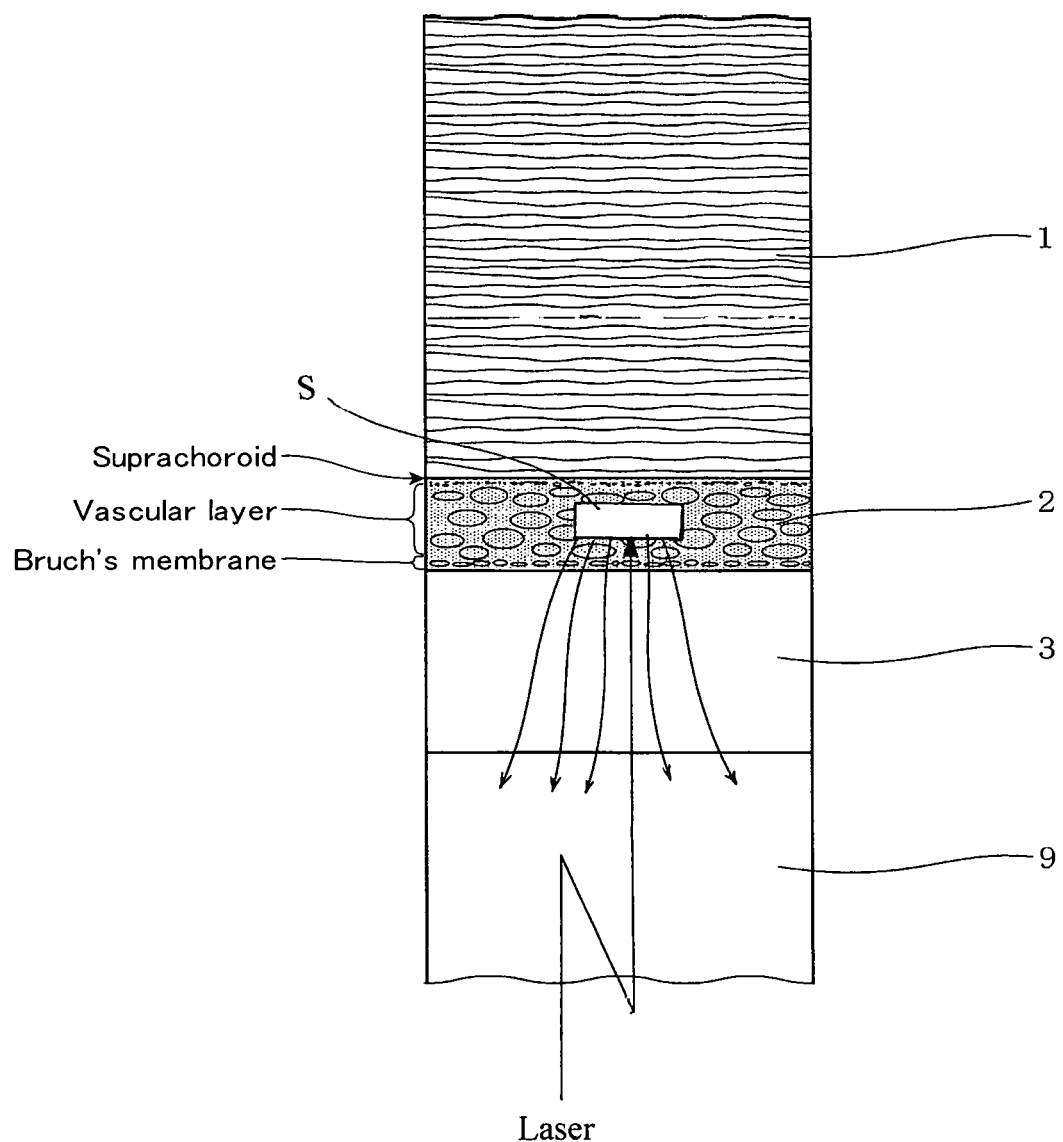
FIG. 1 is a perspective view illustrating an implant according to one embodiment of the invention.

An implant and a method for adjusting the drug release level from the implant according to exemplary embodiments of the invention are described in detail below with reference to the drawings.

The implant according to the embodiment of the invention is used for a human or other animals that have an eyeball, and is used to treat various inflammatory eye diseases and proliferative eye diseases such as exudative age-related macular degeneration (ARMD), cystoid macular edema, diabetic macular edema, uveitis, retinitis, choroiditis, proliferative vieoretinopathy, and proliferative diabetic retinopathy. The implant according to the embodiment of the invention includes a drug and is inserted into part (particularly the choroid) of the eye (i.e., a target part of a living body) to effect sustained release of the drug.

Note that the target into which the implant according to the embodiment of the invention is inserted is not limited to a human. The implant according to the embodiment of the invention may also be applied to various animals (e.g., rabbit, monkey, dog, cat, horse, and cow) having an eyeball structure similar to that of a human.

The implant may include one drug or two or more drugs appropriately selected from an anti-inflammatory drug, an antimicrobial drug, an anticancer drug, an analgesic drug, an antihypertensive drug, an antihyperlipidemic drug, an antidiabetic drug, and the like. The drug includes a steroid drug. The steroid drug may be one steroid drug or two or more steroid drugs selected from cortisone, prednisolone, fluorometholone, dexamethasone, medrysone, loteprednol, fluazacort, hydrocortisone, betamethasone, prednisone, methylprednisolone, triamcinolone hexacetonide, paramethasone acetate, diflorasone, fluocinonide, derivatives thereof, and the like. Note that the steroid drug is not limited thereto. In one embodiment of the invention, dexamethasone is used as the steroid drug. Dexamethasone is a steroid drug that is widely used in medical practice, and is very useful for ophthalmic treatment.

The implant includes a biodegradable polymer. The biodegradable polymer may be one biodegradable polymer or two or more biodegradable polymers selected from polylactic acid, polyglycolic acid, a lactic acid-glycolic acid copolymer, hydroxypropyl cellulose, and the like. Note that the biodegradable polymer is not limited thereto. In one embodiment of the invention, polylactic acid is used as the biodegradable polymer. Polylactic acid is a very useful biodegradable polymer that is generally used in the medical field.

The implant also includes a photoactive agent that accelerates the release of the drug when irradiated with laser light.

The photoactive agent may be one compound or two or more compounds selected from a porphyrin, hematoporphyrin, a hematoporphyrin derivative, pheophorbide, a pheophorbide derivative, benzoporphyrin, a benzoporphyrin derivative, bacteriochlorin, purpurin, merocyanine, porphycene, and a tricarbocyanine. Note that the photoactive agent is not limited thereto. In one embodiment of the invention, indocyanine green (i.e., tricarbocyanine) is used as the photoactive agent. Indocyanine green easily absorbs laser light, and ensures reliable release of the drug.

The implant includes 100 to 500 parts by weight of the biodegradable polymer, and 0.02 to 2 parts by weight of the photoactive agent based on 100 parts by weight of the steroid drug. The implant preferably includes 200 to 400 parts by weight of the biodegradable polymer, and 0.05 to 1 part by weight of the photoactive agent based on 100 parts by weight of the steroid drug. The implant more preferably includes 250 to 350 parts by weight of the biodegradable polymer, and 0.1 to 0.4 parts by weight of the photoactive agent based on 100 parts by weight of the steroid drug. It is preferable to use (mix) dexamethasone, polylactic acid, and indocyanine green (that are used in one embodiment of the invention) in the above ratio.

An example of an implant processing method is described below. For example, the steroid drug, the biodegradable polymer, and the photoactive agent are dissolved in an appropriate organic solvent, and the solution is freeze-dried to obtain a uniform pancake-like product. For example, dioxane is used as the organic solvent when using a combination of dexamethasone, polylactic acid, and indocyanine green. The pancake-like product is compressed using a known press and heated to obtain a columnar product. The columnar product is cut to the desired length to obtain a chip (see FIG. 1).

The diameter D of the implant S (chip) is within the range of 0.05 mm≤D≤0.5 mm, preferably 0.1 mm≤D≤0.3 mm, and more preferably 0.15 mm≤D≤0.25 mm, for example. The length L of the implant S (chip) is within the range of 0.1 mm≤L≤1.0 mm, preferably 0.3 mm≤L≤0.7 mm, and more preferably 0.4 mm≤L≤0.6 mm, for example. The weight W of the implant S (chip) is within the range of 50 µg≤W≤110 µg, and preferably 70 µg≤W≤90 µg. When using a combination of dexamethasone, polylactic acid, and indocyanine green, the implant was cut so that D=0.2 mm, L=0.5 mm, and W=80 µg.

Note that the implant need not necessarily have a columnar shape. For example, the horizontal section of the implant may be elliptical or rectangular.

The laser light conditions are described below. For example, laser light is applied to the implant externally through the crystalline lens using a known laser photocoagulator used for laser light treatment.

For example, laser light having a wavelength of 488 nm to 647 nm is used. For example, argon (Ar) laser light (wavelength: 514 nm) is used as the laser light. When white laser light is used as the laser light, the laser light may not be sufficiently absorbed by the implant. The intensity of the laser light is set to 100 mW to 10 W. For example, the intensity of the laser light is set to 1000 mW. The laser light is applied in a pulsed manner. The spot size (diameter) of the laser light is set to 5 µm to 500 µm. For example, the spot size of the laser light is set to 50 µm. The pulse duration is set to 0.005 seconds to 0.5 seconds. For example, the pulse duration is set to 0.05 seconds. The number of shots of the laser light is appropriately determined depending on the disease state and the like. The release level of the steroid drug changes corresponding to the number of shots. For example, the number of shots is set to 5 to 500.

Figure 2:
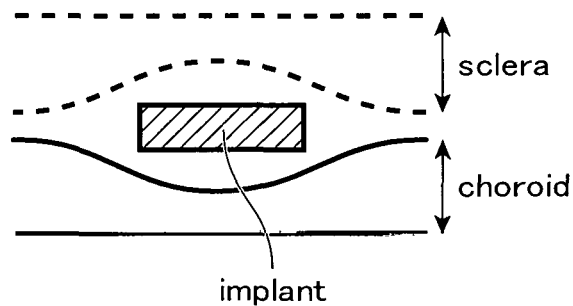
FIG. 2 is a cross-sectional view illustrating a state in which laser light is applied to an implant according to one embodiment of the invention that has been inserted into the choroid of the eye.
Figure 2:
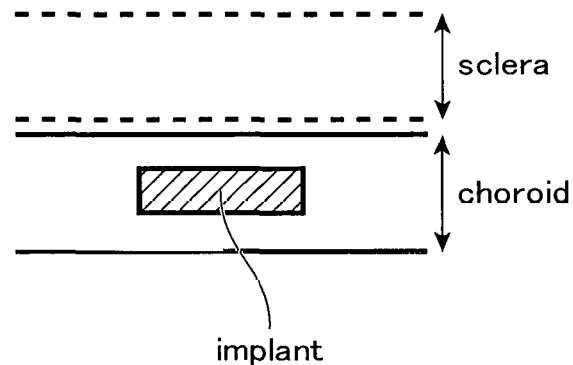
Figure 3:
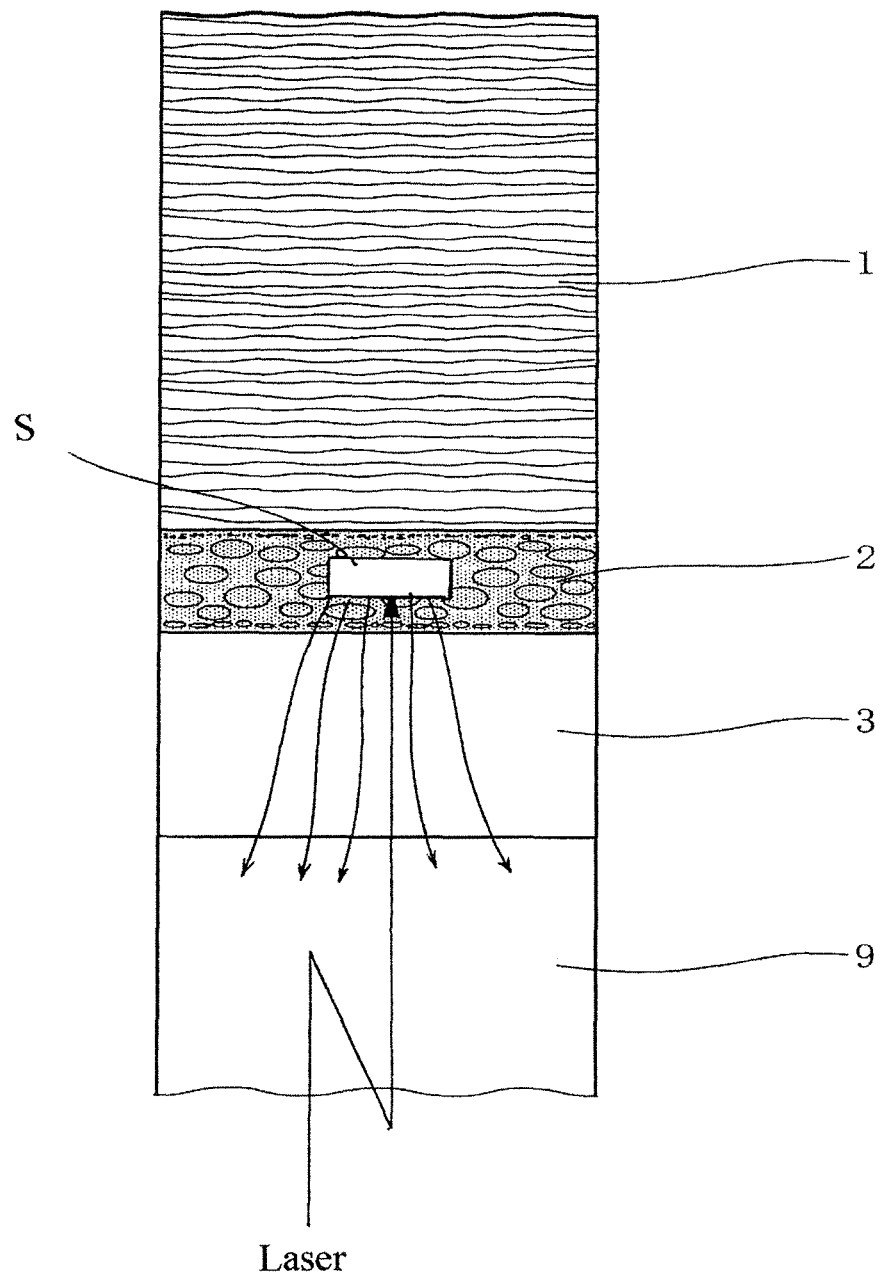
FIG. 3 is an enlarged cross-sectional view illustrating a part into which an implant according to one embodiment of the invention has been inserted.

The implant S according to the embodiment of the invention is inserted into the choroid using the unique implantation method developed by the inventor. As illustrated in FIGS. 2 and 3, an eye consists of an eyeball, adnexa bulbi, and optic nerves. The eyeball consists of outer wall members such as a sclera 1, a choroid 2, a retina 3, a cornea 4, an iris 5, a ciliary body 6, and a Zinn's zonule 7, and content members such as a crystalline lens 8, a vitreous body 9, and an aqueous humor 10. The inner part of the vitreous body 9 is classified into a vitreous gel 9-1, and a liquefied vitreous body 9-2. The liquefied vitreous body 9-2 starts to appear in adulthood (in the case of a human). The vitreous gel 9-1 becomes smaller, and the liquefied vitreous body 9-2 becomes larger with aging. The adnexa bulbi consists of a lacrimal apparatus 11, a conjunctiva 12, and the like. The outer wall of the posterior segment has a three-layer structure in which the sclera 1 forms an outer layer, the choroid 2 forms an intermediate layer, and the retina 3 forms an inner layer. In one embodiment of the invention, the implant is inserted into the choroid 2. The implantation steps are described below.

(A) Vitreous Gel Liquefaction Step

Figure 4:
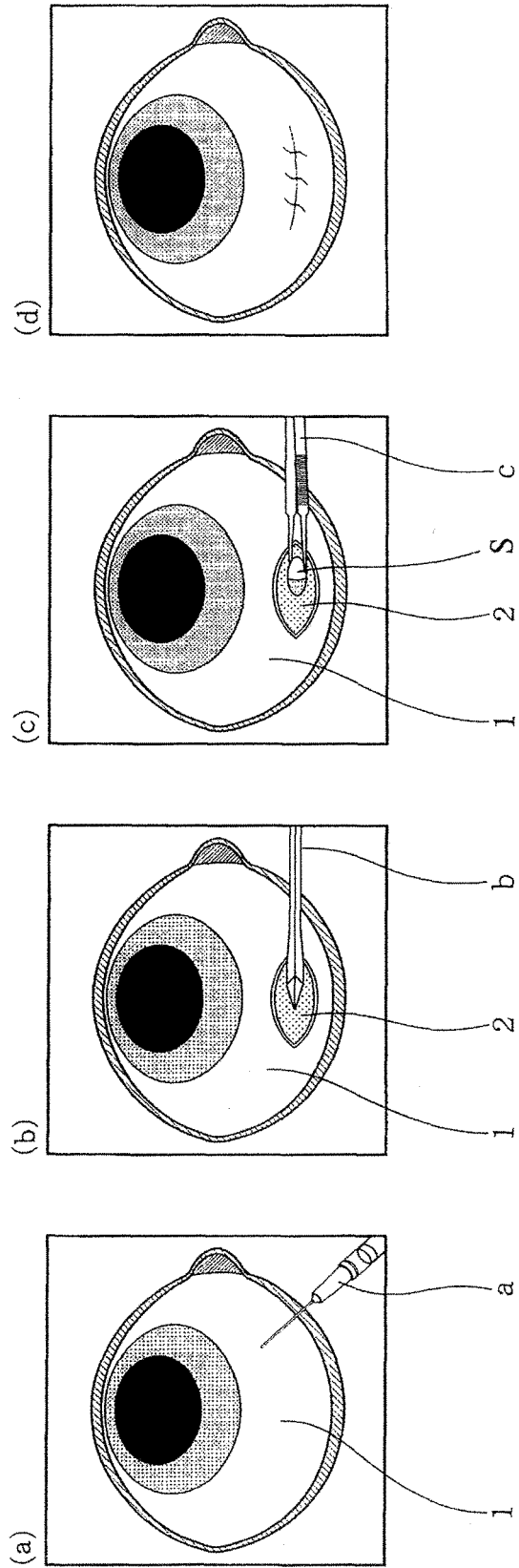
FIG. 4 is a view illustrating an outline of a method for inserting an implant according to one embodiment of the invention into the choroid.

In this step, the vitreous gel is liquefied (see (a) in FIG. 4). The vitreous gel is liquefied by injecting a liquefacient into the vitreous body using a syringe a. A protease may be used as the liquefacient. In this case, the proteins that form the vitreous gel are hydrolyzed to liquefy the vitreous gel. Note that part of the vitreous gel is liquefied in an adult human. The vitreous body can be made softer by liquefying the vitreous gel by this step, and sucking the vitreous gel in the subsequent step. The above state is maintained for 1 to 7 days.

(B) Choroid Exposure Step

When 1 to 7 days has elapsed, the lower part of the conjunctiva is incised under a microscope, and the sclera 1 is incised at a position about 6 mm from the limbus to expose the choroid 2 (see (b) in FIG. 4), for example. The incision operation may be performed using an incision instrument b (e.g., surgical knife).

(C) Vitreous Humor Suction Step

A surgical lens for vitrectomy is placed on the cornea. A syringe needle is inserted from the pars plana while observing the ocular fundus under a microscope, and a specific amount of the vitreous humor is sucked directly above the optic disc. The internal pressure of the vitreous body 9 can thus be reduced to achieve a soft state. The retina thinly peels off from the choroid, and a hole is rarely formed in the retina 3 when incising the choroid 2. Therefore, it is possible to reduce the risk of damage to the retina 3.

(D) Pocket-Forming Step

A pocket for inserting the implant S is formed in the choroid 2. In this case, the incision instrument b is tilted to some extent with respect to the tangential direction, and the tip of the incision instrument b is shallowly inserted into the exposed choroid 2 (see (a) in FIG. 5).

The choroid 2 includes a blood vessel layer that contains a number of blood vessels, and bleeding occurs when the end of the incision instrument b has reached the blood vessel layer. The knife is stopped at a position at which bleeding has occurred, and about 0.5 minutes to about 2 minutes is allowed to elapse to significantly expand the choroid 2 (see (b) in FIG. 5).

Figure 5:
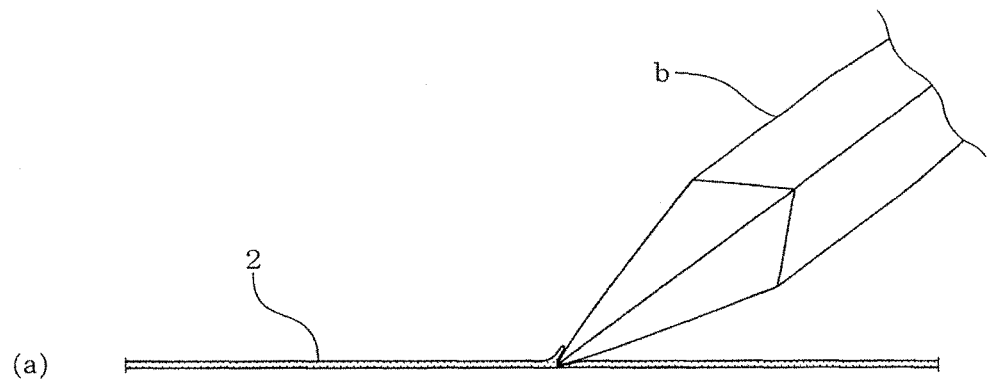
FIG. 5 is a view illustrating incision of the choroid, expansion of the choroid, and formation of a pocket in the choroid when inserting an implant according to one embodiment of the invention into the choroid.
Figure 5:
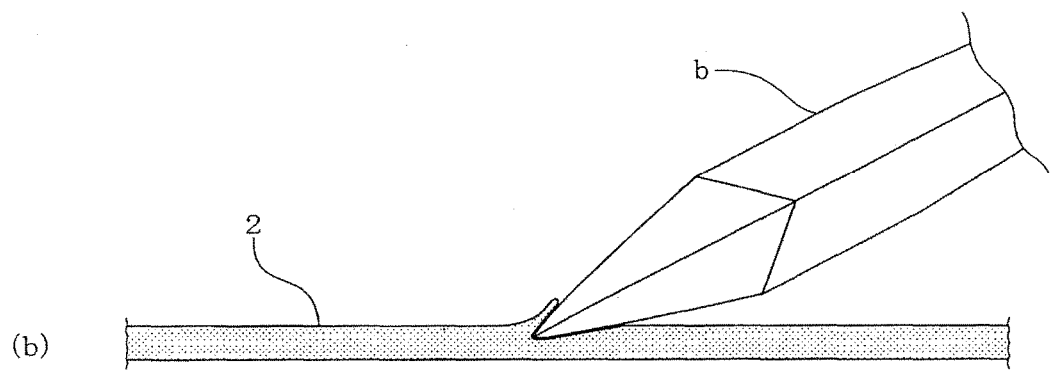
Figure 5:
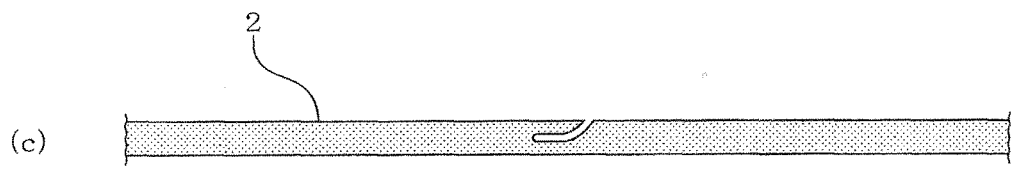

After expanding the choroid 2 for a specific time after inserting the incision instrument b into the choroid 2, the incision instrument b is moved in the choroid 2 parallel to the layer of the choroid 2 (in the tangential direction) to form a pocket in the choroid 2 (see (c) in FIG. 5).

In this case, it is preferable to incise the choroid 2 by moving the incision instrument b parallel to the layer of the choroid 2 (in the tangential direction) at a position corresponding to half of the thickness of the layer of the choroid 2. Note that the incision instrument b may be removed from the choroid 2 when allowing a specific time to elapse after inserting the incision instrument b into the choroid 2.

When forming a pocket in the choroid 2, the incision instrument b (e.g., surgical knife or spatulas) is inserted through the incised area of the choroid 2 to form a pocket (pocket-like space) at a position corresponding to half of the thickness of the layer of the choroid 2.

The pocket is formed to have a size that allows insertion of the implant S. It is preferable to form a square or rectangular cut (side length: about 1 mm to about 2 mm) parallel to the layer of the choroid 2 using the incision instrument. Bleeding is then stopped using a strong hemostatic agent (e.g., epinephrine).

According to the above method for inserting the implant S, since the vitreous gel is sucked to soften the vitreous body after liquefying the vitreous humor, and the pocket is formed after expanding the thin choroid 2 (i.e., increasing the thickness of the choroid 2), the pocket can be easily formed while reducing the risk of damage to the retina 3. Note that the expression "after expanding" used herein does not refer to only a state in which the choroid 2 has been completely expanded, but also refers to a state in which the choroid 2 has been expanded so that the choroid 2 has a thickness larger than the initial thickness by a factor of 2 to 5, for example.

(E) Implant Insertion Step

Figure 6:
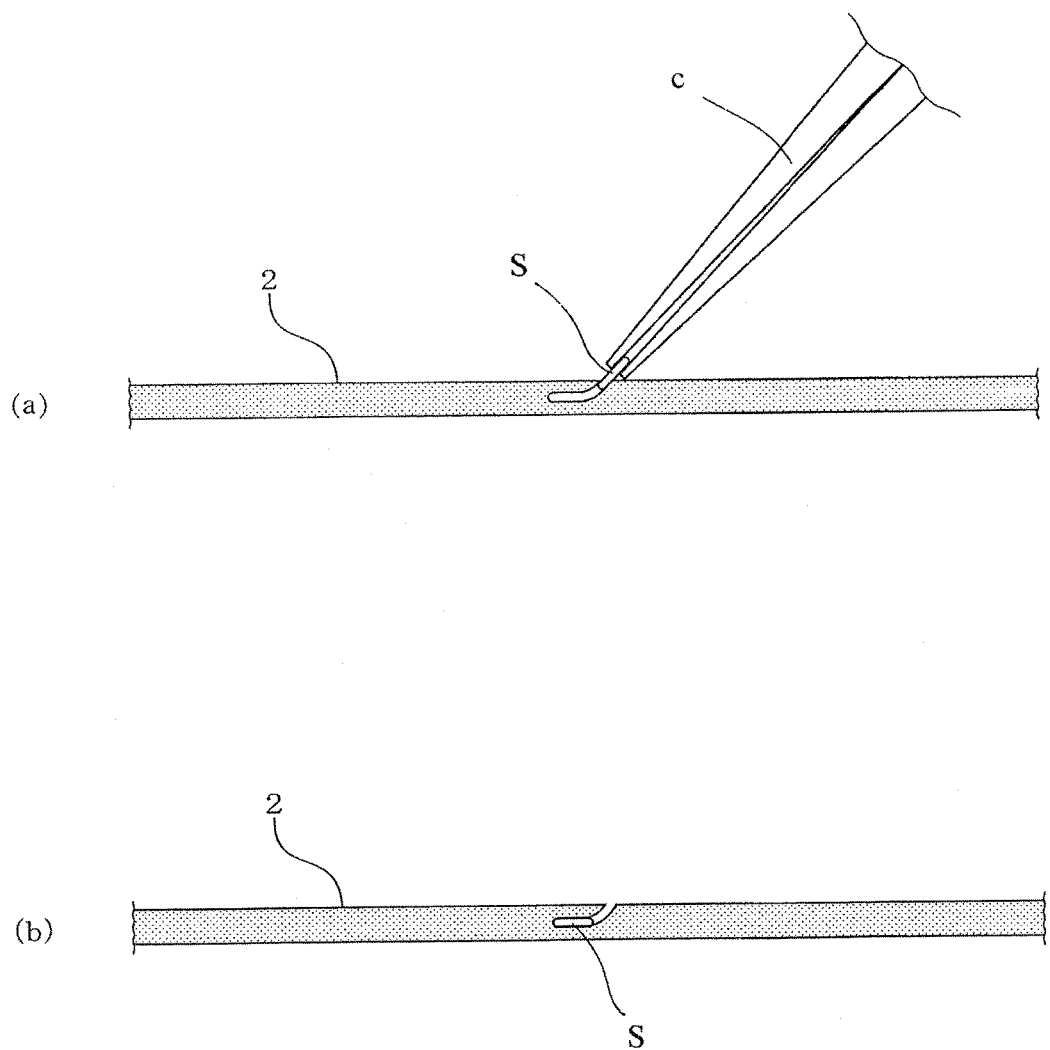
FIG. 6 is a view illustrating a state when inserting an implant according to one embodiment of the invention into the choroid.

In this step, the implant S is inserted into the pocket using forceps c (see (c) in FIG. 4 and (a) and (b) in FIG. 6).

(F) Suture Step

The sclera 1 and the conjunctiva are sequentially sutured, and antibiotic ointment is applied to the eye to complete surgery (see (d) in FIG. 4).

After completion of surgery, the drug is released into the vitreous body 9 from the implant S in a sustained manner (see FIGS. 2 and 3). The method for adjusting the drug release level according to the embodiment of the invention is appropriately performed during this process. For example, laser light is applied to the implant S externally through the crystalline lens 8 using a known laser photocoagulator used for laser light treatment. The laser light is applied in a pulsed manner.

The photoactive agent included in the implant S absorbs the energy from the laser light to accelerate the release of the steroid drug. As a result, the level of the steroid drug in the vitreous body increases. Therefore, the release level of the steroid drug released into the vitreous body 9 can be adjusted by controlling the irradiation intensity of laser light, the irradiation time of laser light, the number of shots, and the like, for example. This makes it possible to perform treatment corresponding to the disease state and the effectiveness of the drug on each individual. In particular, since the laser light is applied in a pulsed manner, it is possible to control the release level by adjusting the pulse number. Specifically, since the photoactive agent accelerates the release of the drug to a different extent corresponding to the pulse number, the level can be easily controlled by changing the pulse number.

Since the implant S is inserted into the choroid 2, it is easy for laser light to position the implant S as compared with the case where the implant S is inserted into the sclera 1, whereby the drug release acceleration effect can be reliably achieved.

EXAMPLES

An implant according to an example of the invention is described below. Dexamethasone (DEX) (manufactured by Sigma Chemical), 20 kDa polylactic acid (poly(DL-lactide) (PLA)) (manufactured by Wako Pure Chemical Industries, Ltd.), and indocyanine green (ICG) (manufactured by Daiichi Seiyaku Co., Ltd.) were used.

50 mg of dexamethasone (DEX), 150 mg of polylactic acid (PLA), and 100 μg of indocyanine green (ICG) were dissolved in 5 mL of dioxane (organic solvent), and the solution was freeze-dried at −80° C. for 48 hours to obtain a uniform pancake-like product. The pancake-like product was compressed using a press and heated to obtain a columnar product. The columnar product was cut to obtain an implant. The implant had a weight of 80 μg, a diameter of 0.2 mm, and a length of 0.5 mm. The dexamethasone content in the implant was 25% (wt/vol).

Test examples are described below.

In the test examples, a laser light irradiation system "NOVUS SPECTRA" (manufactured by Lumenis Co., Ltd.) was used, and argon green laser light (wavelength: 514 nm) was applied. The intensity of the laser light was set to 1000 mW. The spot size (diameter) of the laser light was set to 50 μm. The pulse duration was set to 0.05 seconds.

Test Example 1: In Vitro Dexamethasone Level Measurement

Eight tubes (1.5 ml) charged with 1 ml of physiological saline were provided. The implant according to the example was put in each tube, and pulsed argon green laser light (50 shots) was applied to four tubes among the eight tubes. The dexamethasone level was measured after 1, 2, and 4 weeks by enzyme-linked immunosorbent assay (ELISA).

Figure 7:
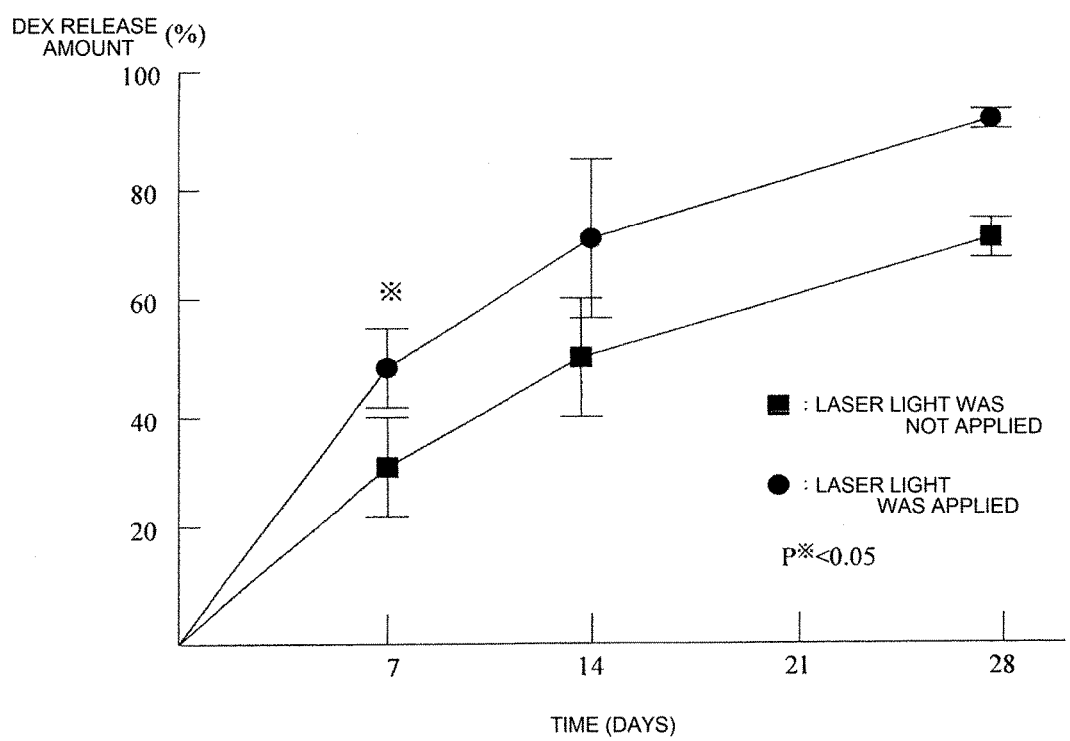
FIG. 7 is a graph showing a change in the dexamethasone level in physiological saline when laser light was applied to the implant according to the example in physiological saline, and when laser light was not applied to the implant according to the example in physiological saline (Test Example 1).

The results are shown in FIG. 7. In FIG. 7, reference sign P indicates a significant difference.

When the laser light was not applied, the dexamethasone (DEX) level gradually increased over about 4 weeks. When the laser light was applied, the dexamethasone (DEX) level significantly increased within the first week, and then gradually increased in the same manner as the control.

The above results demonstrate that the dexamethasone (DEX) level can be adjusted by applying laser light.

Test Example 2: Surgical Procedure of Implant Insertion

Figure 8:
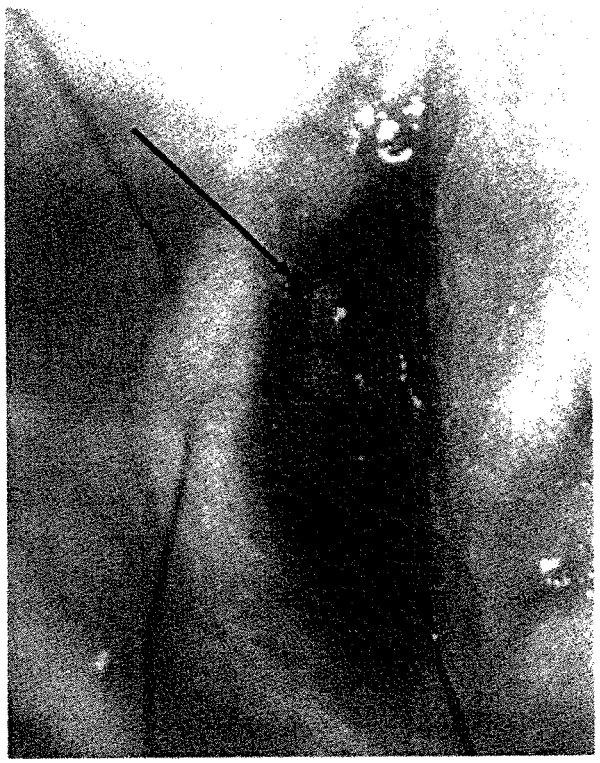
FIG. 8 shows photographs according to Test Example 2, wherein (A) is a photograph (photograph substituted for a drawing) showing the implant according to the example (see the black arrow), and (B) is a photograph (photograph substituted for a drawing) showing a state in which the implant according to the example (see the black arrow) was inserted into the choroid of the eye of the rabbit.
Figure 8:
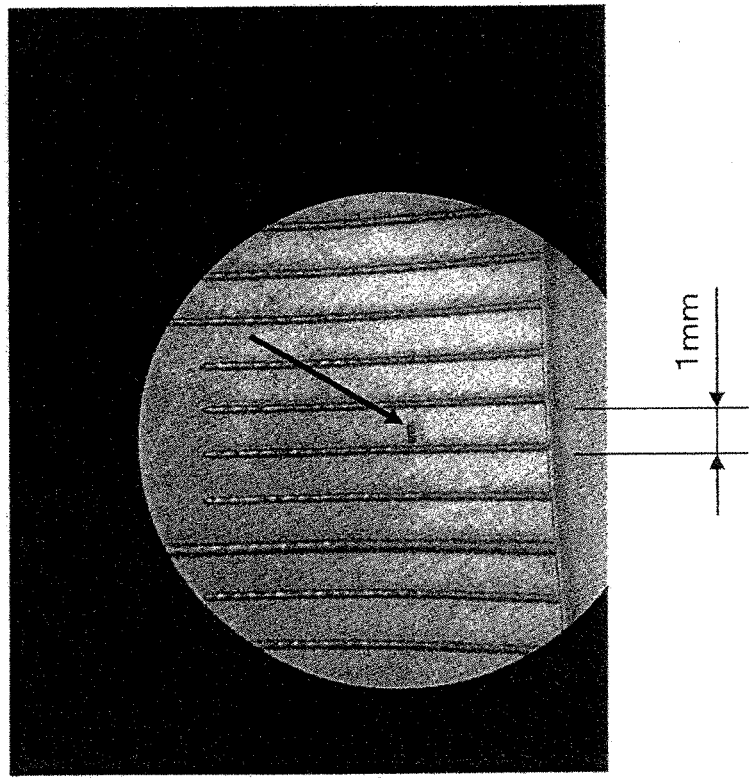

The implant was inserted into a Dutch rabbit under general anesthesia (see FIG. 8). The sclera of the eyeball of the rabbit was incised, the exposed choroid was incised to half of the thickness of the layer of the choroid to create a pocket consisting of an incision, and the implant was inserted into the pocket.

In FIG. 8, (A) is a photograph (photograph substituted for a drawing) showing the implant according to the example. The implant is positioned within the range of 1 mm.

In FIG. 8, (B) is a photograph (photograph substituted for a drawing) showing a state in which the implant according to the example was inserted into the choroid of the eye of the rabbit. The photograph clearly shows a state in which the implant is inserted into the choroid.

Test Example 3: In Vivo Dexamethasone Level Measurement (1)

The relationship between the intensity of the laser light and the dexamethasone (DEX) level in the vitreous body was determined as described below. Twelve Dutch rabbits similar to that used in Test Example 2 were equally divided into three groups (4 in each group). The implant was inserted into each rabbit, and argon green laser light was applied (10 shots, 50 shots, or 200 shots) to the implant. The dexamethasone (DEX) level in the vitreous body was immediately measured by mass spectrometry, and the average dexamethasone (DEX) level was calculated on a group basis.

Figure 9:
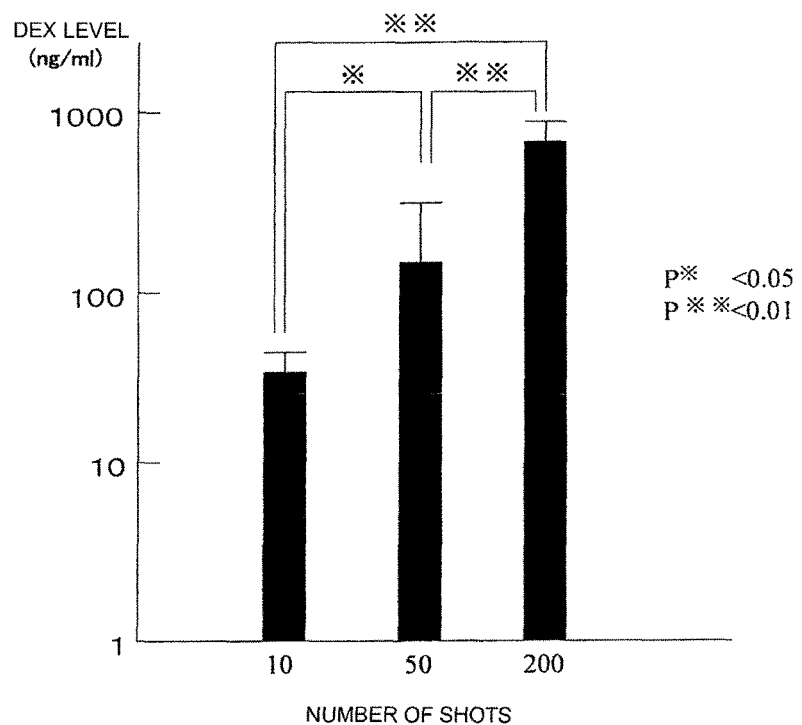
FIG. 9 is a graph showing the relationship between the number of shots of laser light and the dexamethasone level in the vitreous body when the implant according to the example was inserted (Test Example 3).

The results are shown in FIG. 9. In FIG. 9, reference sign P indicates a significant difference.

An increase in the dexamethasone (DEX) level in the vitreous body was observed corresponding to the number of shots of the laser light. The average dexamethasone (DEX) density was 39.4±8.1 ng/ml when the number of shots was 10, 174.2±27.6 ng/ml when the number of shots was 50, and 857.8±80.2 ng/ml when the number of shots was 200 (n=4, mean±SD). A statistical difference was observed among the three groups.

Test Example 4: In Vivo Dexamethasone Level Measurement (2)

The utility of the choroid implant using laser light was determined as described below. Twelve Dutch rabbits similar to that used in Test Example 2 were equally divided into three groups (4 in each group); specifically, three groups of a first group in which an implant that did not include dexamethasone (DEX) was inserted, a second group in which the implant according to the example that included dexamethasone (DEX) was inserted, and a third group in which the implant according to the example that included dexamethasone (DEX) was inserted, and pulsed argon green laser light was applied (50 shots) to the implant. The dexamethasone (DEX) level in the vitreous body was measured by mass spectrometry after 1, 7, 14, and 28 days. The vitreous humor was collected using a syringe. The average dexamethasone (DEX) level was calculated on a group basis.

Figure 10:
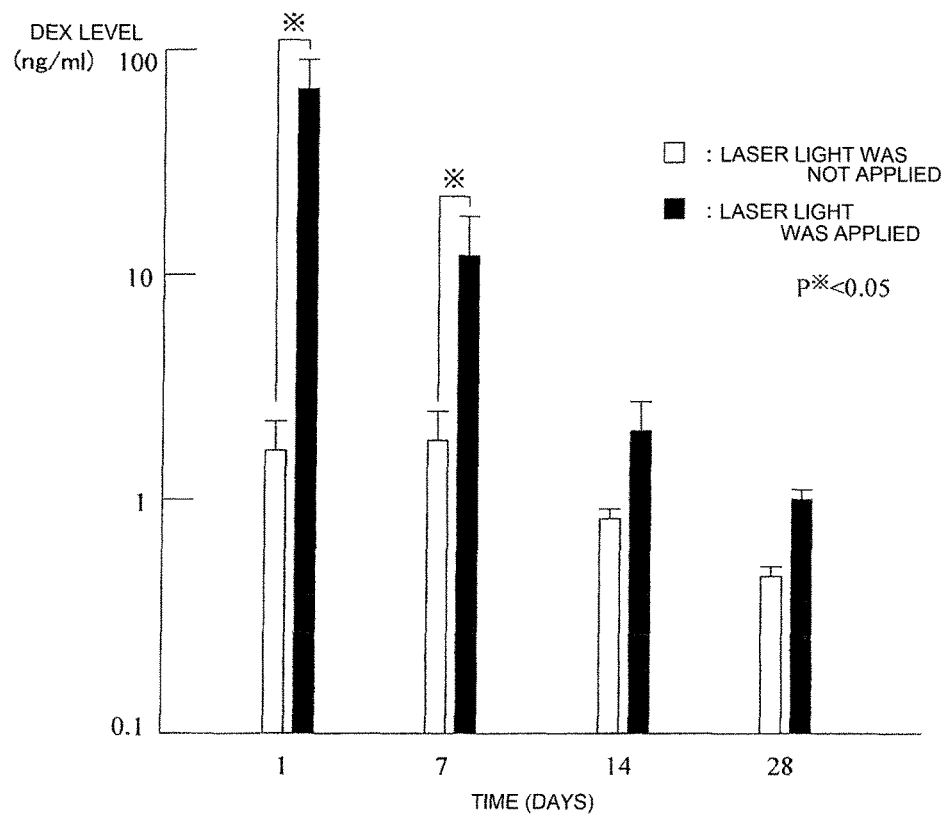
FIG. 10 is a graph showing a change in the dexamethasone level in the vitreous body when laser light was applied to the implant according to the example inserted into the rabbit, and when laser light was not applied to the implant according to the example inserted into the rabbit (Test Example 4).

The results are shown in FIG. 10. In FIG. 10, reference sign P indicates a significant difference.

Dexamethasone (DEX) was not detected from the first group.

The average dexamethasone (DEX) level in the second group after 1, 7, 14, and 28 days was 1.48±0.45 ng/ml, 1.65±0.49 ng/ml, 0.92±0.41 ng/ml, and 0.54±0.42 ng/ml (n=4, mean±SD), respectively.

The average dexamethasone (DEX) level in the third group after 1, 7, 14, and 28 days was 85.0±14.14 ng/ml, 11.58±3.60 ng/ml, 1.97±1.07 ng/ml, and 0.98±0.22 ng/ml (n=4, mean±SD), respectively.

A significant difference was observed between the second group and the third group on the first day and the seventh day. It was confirmed that the dexamethasone (DEX) level could be adjusted by applying the laser light.

Test Example 5: Examination of Ocular Fundus and Tissue

The ocular fundus of each rabbit irradiated with the laser light was examined every week. The eyeball was removed when four weeks had elapsed, and the tissue was examined. In ophthalmoscopically, degeneration was observed in only the part of the retina corresponding to the implant, but no abnormality was observed in the remaining part of the retina. The same observation was obtained by histological examination.

Figure 11:
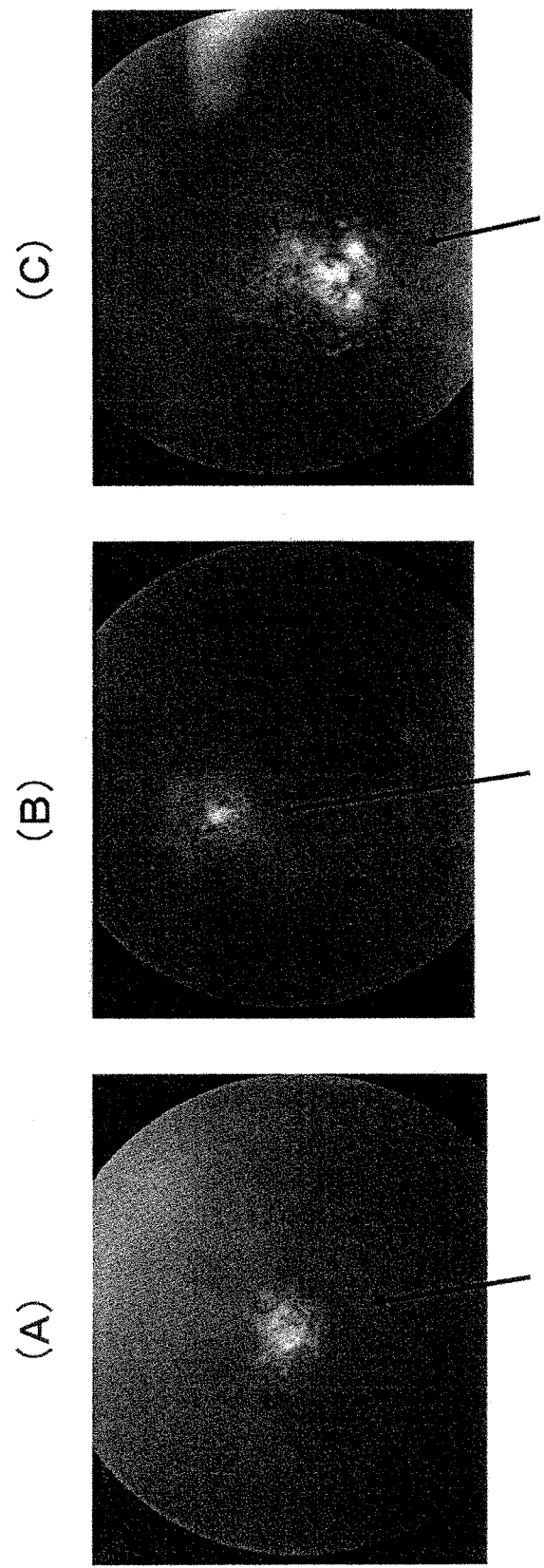
FIG. 11 shows photographs (photographs substituted for a drawing) of the ocular fundus of rabbits, wherein (A) shows the state of the ocular fundus of the rabbit into which the implant (see the black arrow) that did not include dexamethasone was inserted, (B) shows the state of the ocular fundus of the rabbit into which the implant according to the example (see the black arrow) was inserted, and (C) shows the state of the ocular fundus of the rabbit into which the implant according to the example (see the black arrow) was inserted, and which was irradiated with the laser light (Test Example 5).

FIG. 11 shows photographs of the ocular fundus. In FIG. 11, (A) shows the state of the ocular fundus of the rabbit into which the implant that did not include dexamethasone was inserted, (B) shows the state of the ocular fundus of the rabbit into which the implant according to the example was inserted, and (C) shows the state of the ocular fundus of the rabbit into which the implant according to the example was inserted, and which was irradiated with the laser light.

Although the above embodiments have been described taking an example in which the target part of a living body is part of the eye, the target part is not limited thereto. The target part may be a part other than the eye, and may be appropriately changed. The invention is not limited to the above embodiments and examples. Various modifications may be made without materially departing from the scope of the invention.

The invention may suitably be applied when inserting an implant that includes a drug into a living body (e.g., human or pet), and adjusting the release of the drug by applying laser light to treat various diseases, or when performing a clinical trial using experimental animals (e.g., rabbit).

DESCRIPTION OF REFERENCE NUMERALS

S. Implant for human body
1. Sclera
2. Choroid
3. Retina
8. Crystalline lens
9. Vitreous body
a. Syringe
b. Incision
c. Forceps

What is claimed is:

1. A method for adjusting a drug release level from an implant for a living body, comprising:
  incising a choroid parallel to a layer of the choroid at a position corresponding to a half of a thickness of the layer of the choroid in a posterior segment of an eye, thereby forming a pocket in the choroid,
  inserting the implant comprising a drug, a biodegradable polymer, and indocyanine green as a photoactive agent within the pocket, and
  applying laser light to the implant to increase the release level of the drug released into the living body.

2. The method according to claim 1, wherein the laser light is applied in a pulsed manner.

3. The method according to claim 1, wherein the laser light is applied to the implant externally through crystalline lens to release the drug into tissue of the eye and blood to implement treatment of a disease of the eye and/or a whole body.

4. A method for treatment using an implant for a living body, comprising:
- incising a choroid parallel to a layer of the choroid at a position corresponding to a half of a thickness of the layer of the choroid in a posterior segment of an eye, thereby forming a pocket in the choroid,
- inserting the implant comprising a drug, a biodegradable polymer, and indocyanine green as a photoactive agent within the pocket, and
- applying laser light to the implant to increase the release level of the drug released into the living body.

5. The method according to claim 4, wherein a treatment target disease is an eye disease, an inflammatory disease, rheumatism, a collagen disease, hypertension, hyperlipidemia, or diabetes.

6. The method according to claim 5, wherein the eye disease is exudative age-related macular degeneration, cystoid macular edema, diabetic macular edema, uveitis, retinitis, choroiditis, proliferative vitreoretinopathy, or proliferative diabetic retinopathy.

7. The method according to claim 1, wherein the implant comprises 100 to 500 parts by weight of the biodegradable polymer and 0.02 to 2 parts by weight of the photoactive agent based on 100 parts by weight of the drug.

8. The method according to claim 7, wherein the biodegradable polymer is polylactic acid.

9. The method according to claim 1, wherein the drug is steroid.

* * * * *